United States Patent [19]
Ullmark

[11] Patent Number: 5,879,355
[45] Date of Patent: Mar. 9, 1999

[54] DEVICE FOR USE IN TRANSPLANTATION OF BONE TISSUE MATERIAL IN A CAVITY IN BONE

[76] Inventor: Gösta Ullmark, Vallrundan 27, Valbo, S-818 33, Sweden

[21] Appl. No.: 737,612
[22] PCT Filed: May 15, 1995
[86] PCT No.: PCT/SE95/00542
  § 371 Date: Nov. 18, 1996
  § 102(e) Date: Nov. 18, 1996
[87] PCT Pub. No.: WO95/31159
  PCT Pub. Date: Nov. 23, 1995

[30] Foreign Application Priority Data

May 16, 1994 [SE] Sweden ................................ 9401683

[51] Int. Cl.⁶ .................................................. A61B 17/56
[52] U.S. Cl. ................................................ 606/93; 606/92
[58] Field of Search ................................ 606/81, 80, 79, 606/89, 94, 95, 99, 100, 86, 93, 92

[56] References Cited

U.S. PATENT DOCUMENTS

| | | |
|---|---|---|
| 4,116,200 | 9/1978 | Braun et al. ............................ 606/81 |
| 4,662,891 | 5/1987 | Noiles . |
| 4,919,153 | 4/1990 | Chin . |
| 5,116,165 | 5/1992 | Salyer ...................................... 606/81 |
| 5,116,339 | 5/1992 | Glock ...................................... 606/91 |
| 5,192,283 | 3/1993 | Ling et al. . |
| 5,282,804 | 2/1994 | Salyer . |
| 5,358,532 | 10/1994 | Evans et al. . |
| 5,383,932 | 1/1995 | Wilson et al. . |
| 5,385,566 | 1/1995 | Ullmark . |
| 5,413,603 | 5/1995 | Noiles et al. . |
| 5,443,519 | 8/1995 | Averill et al. . |
| 5,480,488 | 1/1996 | Mikhail . |
| 5,527,317 | 6/1996 | Ashby et al. ............................ 606/91 |
| 5,630,819 | 5/1997 | Ashby et al. ............................ 606/86 |
| 5,665,121 | 9/1997 | Gie et al. ................................ 623/16 |

FOREIGN PATENT DOCUMENTS 0 555 004  8/1993  European Pat. Off. .
92/03991  3/1992  WIPO .

Primary Examiner—Guy V. Tucker
Attorney, Agent, or Firm—Browdy and Neimark

[57] ABSTRACT

A device for use in transplantation of bone tissue material (3) in a cavity (2) in bone comprises a surface (1) for compacting the bone tissue material in the cavity. The compacting surface has a relief like structure on its compacting surface (4) for contact with the bone tissue material.

9 Claims, 2 Drawing Sheets

DEVICE FOR USE IN TRANSPLANTATION OF BONE TISSUE MATERIAL IN A CAVITY IN BONE

FIELD OF THE INVENTION AND PRIOR ART

This application is filed under 35 USC 371 based on PCT/SEQ/00542 filed on May 15, 1995.

This invention relates to a device for use in transplantation of bone tissue material in a cavity in bone, said device comprising means for compacting the bone tissue material in the cavity.

In my published Swedish patent applications No. 9200501-6 and 9300572-6, a device of the kind being related to above is described. The object of the transplantation is to give the cavity a desired shape with a required thickness of the bone material forming the wall of the cavity. In the prior patent applications, pretreatment in such orthopaedic surgical operations in which a portion of a prosthesis shall be inserted into said cavity and be secured therein is described as a possible application. Bone cement is then utilised for the securing between the prosthesis portion and the wall of the cavity defined by the bone tissue material.

A particularly preferred application according to my prior Swedish patent applications relates to preparation of cavities in femurs as to receive a portion of a hip joint prosthesis. However, it was pointed out that the invention thereby related to could be applied also in other cases where arbitrary prostheses, for example joint prostheses, are to be applied in a bone of the individual.

The invention according to the present application as well as the invention aspects treated in my prior Swedish patent applications are based upon that a bone transplant formed by a bone tissue material is inserted into the cavity, said bone tissue being present in the bone transplant in the form of a plurality of small pieces or particles, i.e. in a ground or finely divided state. The bone tissue material is brought into a suitable consistency, such as paste or pulp. The bone tissue material then contains a suitable liquid. This liquid may comprise tissue liquid, such as blood. The liquid comprises suitably also water. Furthermore, the liquid may include fat, preferably in the form of living tissue.

The present invention is based upon the knowledge of that the compacting of the bone tissue material into the cavity, which is of considerable importance for the transplantation, is difficult to accomplish as the bone transplant comprises fat and blood tends to flow into the bone transplant from the bottom side. As one then tries to accomplish the compaction of the bone transplant by means of the compacting means, said transplant tends to displace itself upwards along the sides of the compacting means instead of letting itself get compacted effectively deeper in the cavity. These problems are present in the application primarily related to according to my prior patent applications, that is for the preparation of cavities in femurs for the purpose of receiving hip joint prostheses, as well as in the application primarily foreseen in the present invention, that is bone transplantation in a joint socket. This joint socket may for instance be intended to receive the joint ball of a hip joint prosthesis.

When bone losses have led to the need of joint transplantation in a joint socket with ground bone transplant, this has, until now, taken place by means of compacting means presenting an even, outer spherical surface. When the joint socket has been filled up to a required degree with grinded bone transplant, the compacting means has been applied to the transplant and struck or pressed down into that same, the transplant being subjected to compaction and forming itself according to the joint socket in its lower limitation and forming itself according to the compacting means in its upper limitation. Thereby, the compacting surface of the compacting means has a shape corresponding to the ball aimed at cooperation with the joint socket. The problems consisting of the tendency of bone transplant to displace itself out of the joint socket has already been mentioned above.

SUMMARY OF THE INVENTION

The object of the present invention is to further develop prior technique so that the compacting means is designed in a way to make it capable of exerting an effective compacting effect while avoiding the bone transplant from tending to get pressed out of the cavity along the sides to an unacceptable degree. It is emphasised that the compacting means thereby is intended to make bone transplantation possible in all sorts of present cavities in bones, i.e. not only joint sockets of the kind discussed above. Accordingly it is particularly noted that the invention here aimed at also can find its application at the compacting means cited in my Swedish patent applications 9200501-6 and 9300572-6.

The object according to the invention is primarily provided for as the compacting means has a relief like structure on its compacting surface for contact with the bone tissue material. The object of this relief like structure is to obstruct the bones transplant from gliding or displacing along the compacting surface and going out of the cavity around the compacting means. In other words, the relief like structure will accordingly tend to act entrainingly upon the bone transplantation material.

With relief like structure one here relates to a structure presenting ridges and recesses following each other alternatingly to make the compacting surface of the compacting means tend to entrain the transplantation material located nearest to the compacting means.

It is particularly preferred that the relief like structure is at least partly formed by grooves.

According to a further preferred embodiment of the invention, the compacting means has a collar which extends fully or partly around the compacting surface to counteract displacement of transplantation material out of the cavity during the compaction.

Of course, the compacting means according to the invention is provided in different sizes in accordance with the size of the cavity aimed at and the size of which will be defined by the compacting means, and, besides, the collar of the compacting means may also have a varying shape in accordance with the shape of the bone material portions surrounding the joint socket or other cavity which is to be repaired by means of a transplant.

Further preferred embodiments of the compacting means are defined in the dependent patent claims.

BRIEF DESCRIPTION OF THE DRAWINGS

With reference to the appended drawings, below follows a specific description of an embodiment of the invention cited as an example.

In the drawings.

DETAILED DESCRIPTION OF A PREFERRED EMBODIMENT

Figure 3:
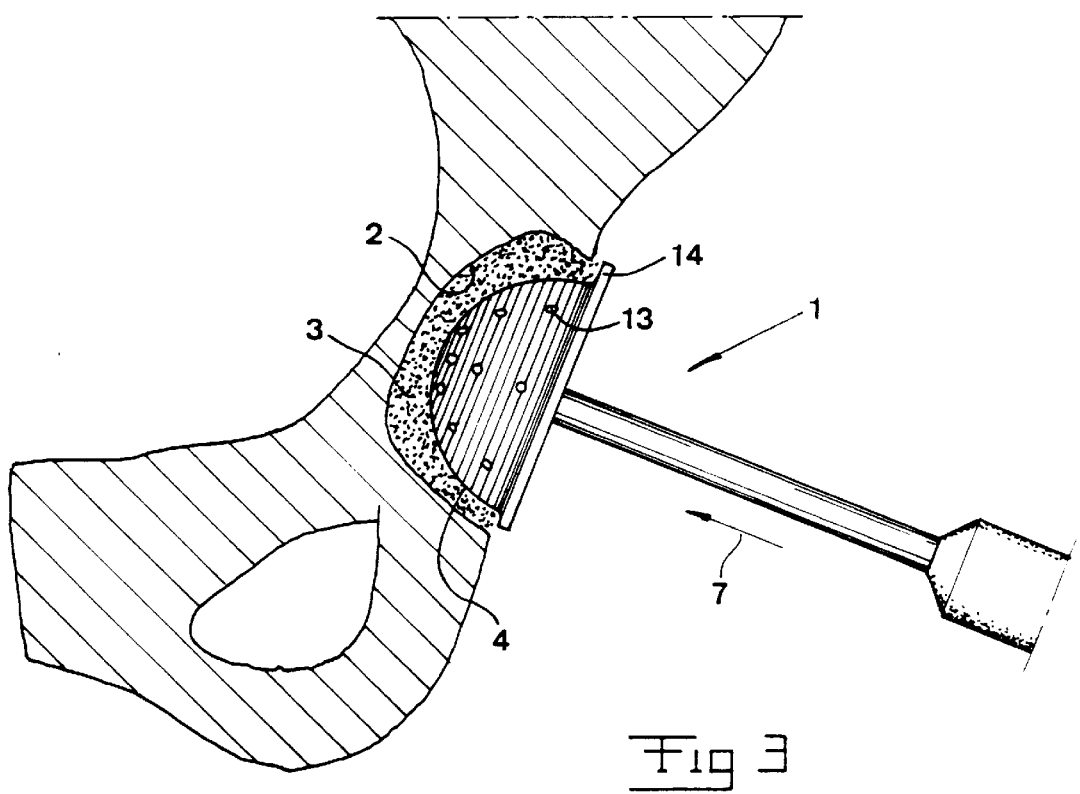
FIG. 3 is a schematic view illustrating the compacting means in function for the compaction of bone tissue material in a cavity in a bone.

The device according to the invention comprises a means 1 for the compaction of the bone tissue material in the cavity in question and more closely illustrated in the drawing figures. In FIG. 3 a joint socket in the hip bone of a patient is illustrated as a cavity 2. This joint socket has, through bone losses, been widened up to an undue degree and might even have been perforated somewhere, in general in the bottom of the socket. In FIG. 3 it is shown how the bone tissue material 3 may be compacted in the cavity 2 by means of the compacting means 1 to make the compacting means leave a joint socket in the hip bone after the execution of the compaction, said joint socket having a satisfactory wall thickness. After a certain period an intergrowth between the bone material of the hip bone and the transplantation material has taken place.

The compacting means 1 has a relief like structure on its compacting surface 4 for contact with the bone tissue material 3. This relief structure comprises ridges 5 and recesses 6 having the task of acting entrainingly upon the transplantation material during the execution of the compaction.

The ridges 5 and recesses 6 should at least partly be orientated on the compacting surface 4 to extend crossways or at least with an angle to the relative direction of movement between the compacting means and the bone transplantation material during the execution of the compaction for the obtaining of the discussed entraining effect upon the transplantation material.

According to a particular preferred embodiment of the invention, the relief like structure is at least partly formed as grooves which form said ridges and recesses respectively. The grooves extend generally transversely to the direction (arrow 7 in FIG. 3) of insertion of the compacting means into the cavity 2.

The compacting surface 4 of the compacting means forms a projection. The grooves 5, 6 extend fully or partly around the projection 4 on its outer surface. In practice it is preferred that the grooves extend circularly on the compacting surface 4 in planes generally perpendicular to the extension direction of the projection 4 and, accordingly, perpendicular to the direction (arrow 7) of insertion of the compacting means into the cavity 2.

When the compacting means 1 is to serve for the bone transplantation in a joint socket it is preferred that the projection has a generally part-spherical shape. More specifically, the projection 4 may have the character of a half sphere.

On the compacting surface 4 the grooves form step formations with step surfaces 8 which to a major degree extend along the lengthwise axle 9 of the compacting means. The step formations further comprise step surfaces 10 which to a major degree extend radially in relation to the lengthwise axle 9 of the compacting means.

Figure 1:
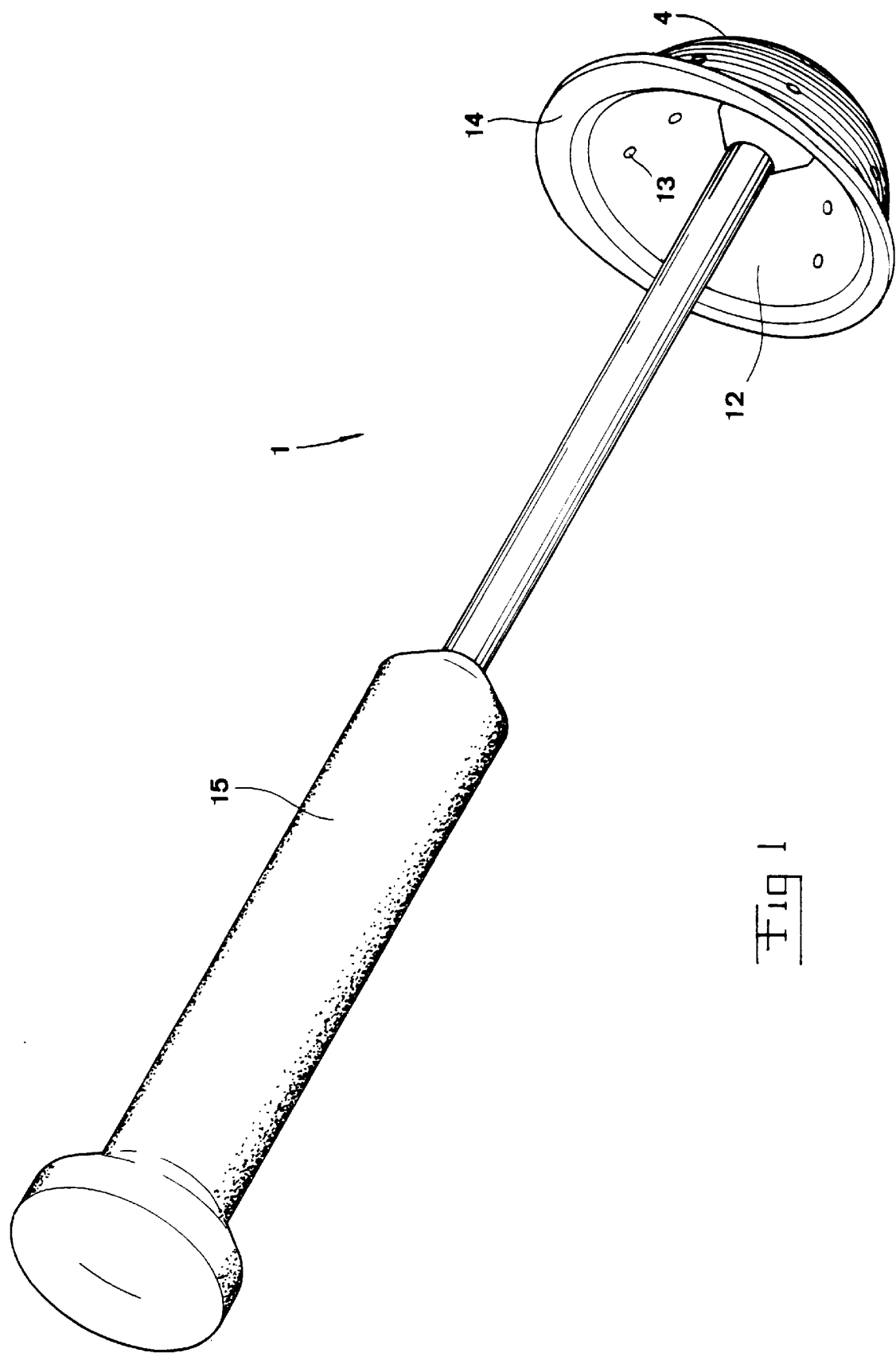
FIG. 1 is a perspective view of the compacting means according to the invention.
Figure 2:
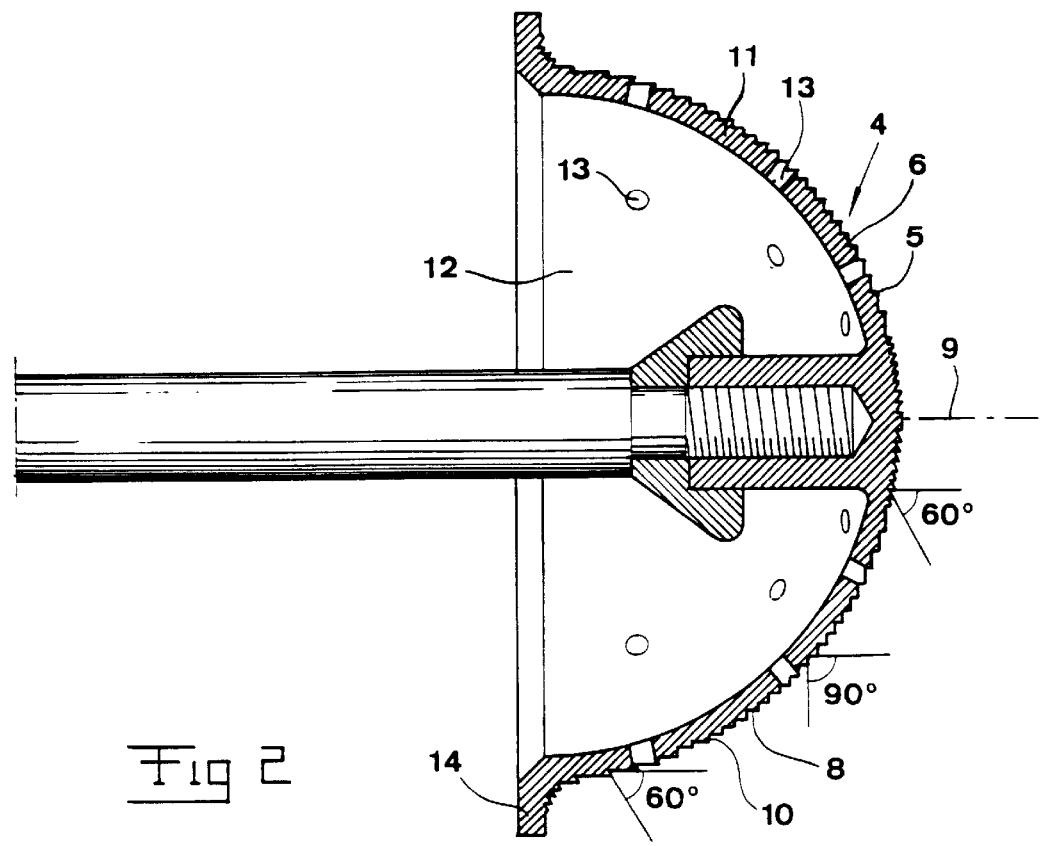
FIG. 2 is a length section through a jacket defining the compacting surface of a compacting means.

According to a possible embodiment of the invention the step surfaces 8 may be generally axially extending while the step surfaces 10 extend generally radially. However, variations are possible within the frame of the idea of the invention here aimed at; as can be seen in FIG. 2, the angle between adjoining step surfaces 8 and 10 may vary. Through such a variation of angle the entraining effect of the compacting means to the transplantation material can be adapted as requested.

The compacting surface 4 of the compacting means is defined by a jacket 11, which has an inner cavity 12. The jacket 11 is provided with openings 13 for allowing liquid to pass from the surrounding bone tissue material through the jacket 11 and into the cavity 12. From this cavity 12 the liquid can flow away thanks to the effect of the gravitational force or, alternatively, any known water suction equipment may be used to suck away the excessive liquid. The departure of liquid from the transplant means a consolidation of the same and a reduced tendency of the transplant to unintentionally diverge to the sides.

The compacting means 1 has a collar 14, which extends fully or partly around the compacting surface 4 to counteract the displacement of transplantation material out of the cavity 2 during the compaction. As can be seen in the figures, the collar 14 has the character of a radially projecting flange and it may have, in correspondence with the intended use of the compacting means, different radial projection length out from the compacting surface 4 along the periphery of the latter.

The very jacket 11 of the compacting means has the character of a hollow bowl.

The compacting means 1 has a handle 15 which is fastened to the jacket 11 in the bottom of the cavity 12 of the latter. This handle 15 should be designed for allowing striking thereon to effectively press the compacting means against the bone transplant.

During use of the compacting means according to the invention the bone transplant is first arranged in the cavity 2 in question. Thereafter a compacting means with a shape suited for the purpose is chosen and the bone transplant is compacted by means of the compacting means to a required degree. The relief like structure on the compacting surface 4 of the compacting means reduces the tendency of the bone transplant to glide away and this effect is promoted by the collar 14 of the compacting means. As liquid can go away from the bone transplant through the openings 13 arranged in the compacting means, a consolidation of the bone transplantation material takes place and the tendency thereof to unintentionally glide away along the sides of the compacting means from the bottom area in the cavity 2 during the compaction is reduced. When the requested cavity has been created in the bone by means of the transplantation material, the member, for example a joint ball, which is to be received in the cavity can be arranged in its place and the operation be finished. A transplantation executed in this way can possibly immediately be subjected to a load via the joint ball, for example such load that arises during walking, or one can also, so as to be on the safe side, permit a certain period of intergrowth of the transplantation material before such loading.

As already has been noted, the idea of the invention is not at all constricted to compacting means with a shape suited for creating cavities suited for joint balls. On the contrary, the compacting means may have other shapes for the creation of other types of cavities in bones. Also other modifications are possible within the frame of the invention here related to.

I claim:

1. A bone transplantation device to be used prior to placing a prosthesis in a cavity (2) in bone for compacting bone tissue material (3) in the cavity (2) when the device is moved in an insertion direction; the device comprising:

a compacting surface (4) including a relief structure further comprising compacting means for carrying the bone tissue material in the insertion direction when the device is moved in the insertion direction and for leaving the bone tissue material in a compacted state in the cavity during removal of the relief structure from the cavity;

the relief structure further including first step surfaces (10), substantially all of the the first step surfaces being disposed substantially perpendicular to the insertion direction, and second step surfaces (8) generally perpendicular thereto, whereby substantially all of the second step surfaces are aligned to the insertion direction.

2. The device according to claim 1, wherein the compacting surface (4) comprises a projection.

3. The device according to claim 2, wherein the projection includes a generally part-spherical shape.

4. The device according to claim 1, wherein the step extend at least partly around the projection.

5. The device according to claim 1, wherein the compacting surface has a generally part-spherical shape.

6. The device according to claim 1, wherein the compacting surface (4) is defined by a jacket (11) which includes an inner cavity (12), and the jacket includes openings (13) for allowing liquid to pass from the surrounding bone tissue material, through the jacket, and into the cavity.

7. The device according to claim 6, wherein a handle (15) is fastened to the jacket (11) of the compacting means (1) in a bottom of the inner cavity (12).

8. The device according to claim 1, wherein the compacting means (1) includes a collar (14) which extends at least partly around the compacting surface (4) to counteract displacement of transplantation material out of the cavity during compaction.

9. The device according to claim 1, comprising a handle (15).

* * * * *